(12) United States Patent
Pak et al.

(10) Patent No.: US 10,258,395 B2
(45) Date of Patent: Apr. 16, 2019

(54) BONE PLATE LOCKING MECHANISM

(71) Applicant: Stryker European Holdings I, LLC, Kalamazoo, MI (US)

(72) Inventors: Chulho Pak, Ewing, NJ (US); Stephen Gilbert, West Chester, PA (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 392 days.

(21) Appl. No.: 14/863,926

(22) Filed: Sep. 24, 2015

(65) Prior Publication Data

US 2016/0089191 A1   Mar. 31, 2016

Related U.S. Application Data

(60) Provisional application No. 62/055,184, filed on Sep. 25, 2014.

(51) Int. Cl.
*A61B 17/80* (2006.01)

(52) U.S. Cl.
CPC ...... *A61B 17/8047* (2013.01); *A61B 17/8052* (2013.01)

(58) Field of Classification Search
CPC ............ A61B 17/8042; A61B 17/8047; A61B 17/8052
See application file for complete search history.

(56) References Cited

U.S. PATENT DOCUMENTS

| | | |
|---|---|---|
| 5,601,553 A | 2/1997 | Trebing et al. |
| 6,096,040 A | 8/2000 | Esser |
| 6,206,881 B1 | 3/2001 | Frigg et al. |
| 6,322,562 B1 | 11/2001 | Wolter |
| 6,730,091 B1 | 5/2004 | Pfefferle et al. |
| 6,955,677 B2 | 10/2005 | Dahners |
| 6,974,461 B1 | 12/2005 | Wolter |
| 7,179,260 B2 | 2/2007 | Gerlach et al. |
| 7,722,653 B2 | 5/2010 | Young et al. |
| 7,905,910 B2 | 3/2011 | Gerlach et al. |
| 7,909,858 B2 | 3/2011 | Gerlach et al. |
| 8,075,561 B2 | 12/2011 | Wolter |
| 8,105,367 B2 | 1/2012 | Austin et al. |
| 8,382,807 B2 | 2/2013 | Austin et al. |
| 8,870,931 B2 * | 10/2014 | Dahners ............ A61B 17/8047 606/289 |
| 9,433,454 B2 * | 9/2016 | Paolino ............ A61B 17/8057 |
| 2005/0165400 A1 | 7/2005 | Fernandez |

(Continued)

FOREIGN PATENT DOCUMENTS

| | | |
|---|---|---|
| DE | 4343117 A1 | 6/1995 |
| DE | 19629011 A1 | 1/1998 |
| EP | 1649819 A1 | 4/2006 |

OTHER PUBLICATIONS

Extended European Search Report for Application No. EP 15002760 dated Jan. 26, 2016.

*Primary Examiner* — Anu Ramana
(74) *Attorney, Agent, or Firm* — Lerner, David, Littenberg, Krumholz & Mentlik, LLP (57) ABSTRACT

A bone plate locking mechanism and methods for utilizing same are disclosed. A bone plate in accordance with the present invention includes a bone screw hole having a plurality of first lips and a plurality of second lips. The first lips are closer to the upper surface than the second lips and the first and second lips are offset around the bone screw hole.

17 Claims, 8 Drawing Sheets

(56) References Cited

U.S. PATENT DOCUMENTS

| | | |
|---|---|---|
| 2008/0208259 A1 | 8/2008 | Gilbert et al. |
| 2009/0048605 A1 | 2/2009 | Yurek |
| 2009/0076553 A1 | 3/2009 | Wolter |
| 2009/0143824 A1 | 6/2009 | Austin et al. |
| 2010/0256686 A1 | 10/2010 | Fisher et al. |
| 2011/0282393 A1 | 11/2011 | Gerlach et al. |
| 2012/0109216 A1 | 5/2012 | Austin et al. |
| 2012/0323284 A1 | 12/2012 | Baker et al. |
| 2013/0023939 A1* | 1/2013 | Pischl ................ A61B 17/8047 606/286 |
| 2013/0172943 A1 | 7/2013 | Austin et al. |
| 2014/0214092 A1 | 7/2014 | Wolter |
| 2015/0066095 A1 | 3/2015 | Austin et al. |
| 2015/0142063 A1 | 5/2015 | Austin et al. |

\* cited by examiner

BONE PLATE LOCKING MECHANISM

CROSS-REFERENCE TO RELATED APPLICATIONS

The present application claims the benefit of the filing date of U.S. Provisional Patent Application No. 62/055,184 filed Sep. 25, 2014, the disclosure of which is hereby incorporated herein by reference.

BACKGROUND OF THE INVENTION

The present invention pertains to orthopedic bone plates, and in particular, orthopedic bone plates with screw locking features.

A common method utilized in repairing fractures of bones includes affixing bone plates to the bone with screws. Generally, the plates are oriented so that portions thereof are placed on either side of the fracture and screws are placed through bone screw holes of each bone plate portion. Depending upon the particular anatomical area of the fracture, different plate designs exist. For instance, plates designed for use on the distal and proximal portions of long bones such as the femur or tibia may include a shaft and a head, each with screw holes extending therethrough.

One commonly encountered issue with standard bone plate and screw constructs is the tendency for the screws to back out of plate holes after implantation. This not only has the ability to affect the strength of the bone plate construct, but also may cause pain or discomfort in the patient. Often times, additional surgery is required to address screw back out issues. Plate and screw designs have attempted to address this issue by including, inter alia, threaded plate holes that are engaged by the threaded head of a screw or even deformable/deflectable screw hole portions. The aim of such designs is to essentially affix the screw in the hole, thereby preventing back out.

Another common issue with standard bone plate and screw constructs is the inability of the screws to be positioned in a manner in which proper bone purchase can be achieved. In other words, it is often necessary to place the screws along a particular trajectory in order to direct them into portions of the bone that are healthy and capable of holding a screw. This issue has been addressed by allowing for screws to be placed at different angles in bone screw holes (i.e., polyaxially).

There exists a need for a bone plate which addresses each of the aforementioned issues, while also allowing for ease of use by a surgeon or other medical professional.

BRIEF SUMMARY OF THE INVENTION

A first aspect of the present invention is a bone plate including a body having upper and lower surfaces and a bone screw hole formed through the body and including a plurality of first lips and a plurality of second lips. The first lips are closer to the upper surface than the second lips and the first and second lips are offset around the bone screw hole.

The bone plate of the first aspect may include a design in which the first and second lips do not overlap each other or partially overlap each other. The first and second lips may include ramped surfaces, and the bone screw hole may further include a countersink. The bone plate discussed above may be packaged or offered with a bone screw having a head and a shank. In certain embodiments, the bone screw may be of a harder material than bone plate, in particular, the head may be of a harder material than the first and second lips. Placement of the bone screw through the bone plate may result in a deformation or deflection of the first and second lips.

A second aspect of the present invention is a bone plate system including a body, a bone screw hole formed through the body including a plurality of upper and lower lips and a bone screw having a head and a shank. The head may deform or deflect the upper and lower lips upon insertion of the screw through the bone screw hole.

In other embodiments, the upper and lower lips may be offset from each other around the bone screw hole, for instance, offset thirty degrees from each other. In still further embodiments, the first and second lips do not overlap each other. The first and second lips may partially overlap each other or not overlap each other. The first and second lips may include ramped surfaces. The bone screw hole may further include a countersink. The bone screw may be of a harder material than bone plate, in particular, the head portion.

Yet another aspect of the present invention is another bone plate system. The system according to this aspect includes a body, a bone screw hole formed through the body including a plurality of ramped upper and lower lips and a bone screw having a head and a shank. The head is of a harder material than the upper and lower lips and deforms or deflects the upper and lower lips upon insertion of the bone screw in the bone screw hole.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

Figure 1:
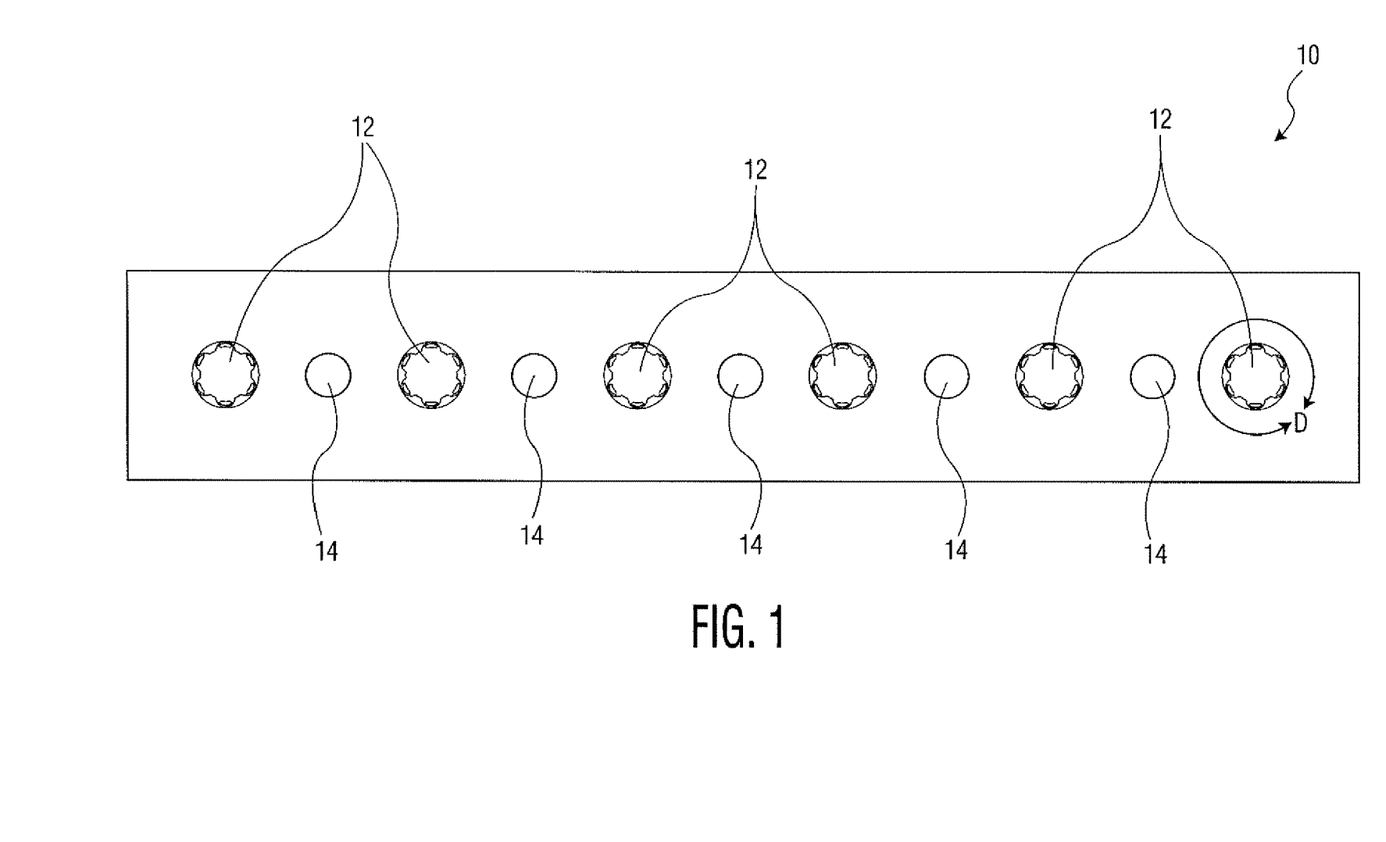
FIG. 1 is a top view of a bone plate according to an embodiment of the present invention.
Figure 2:
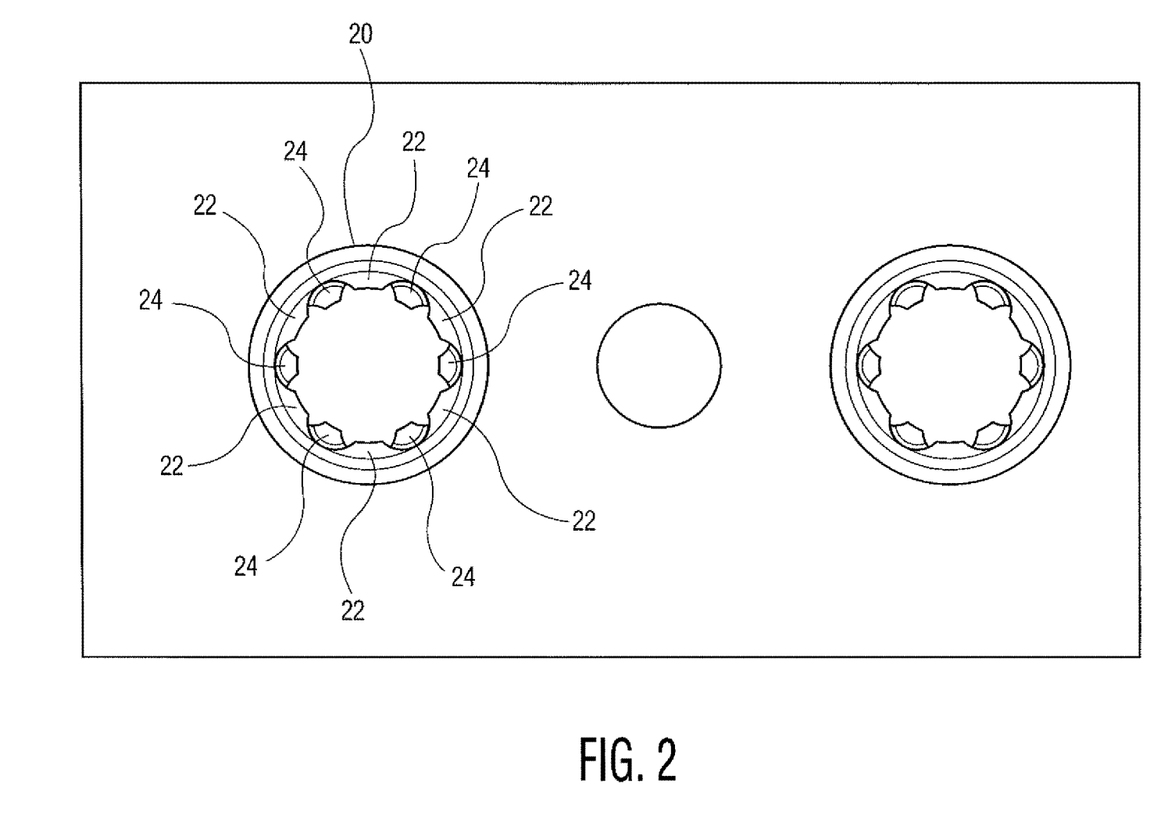
FIG. 2 is another top view of the bone plate of FIG. 1 focusing on two holes thereof.
Figure 3:
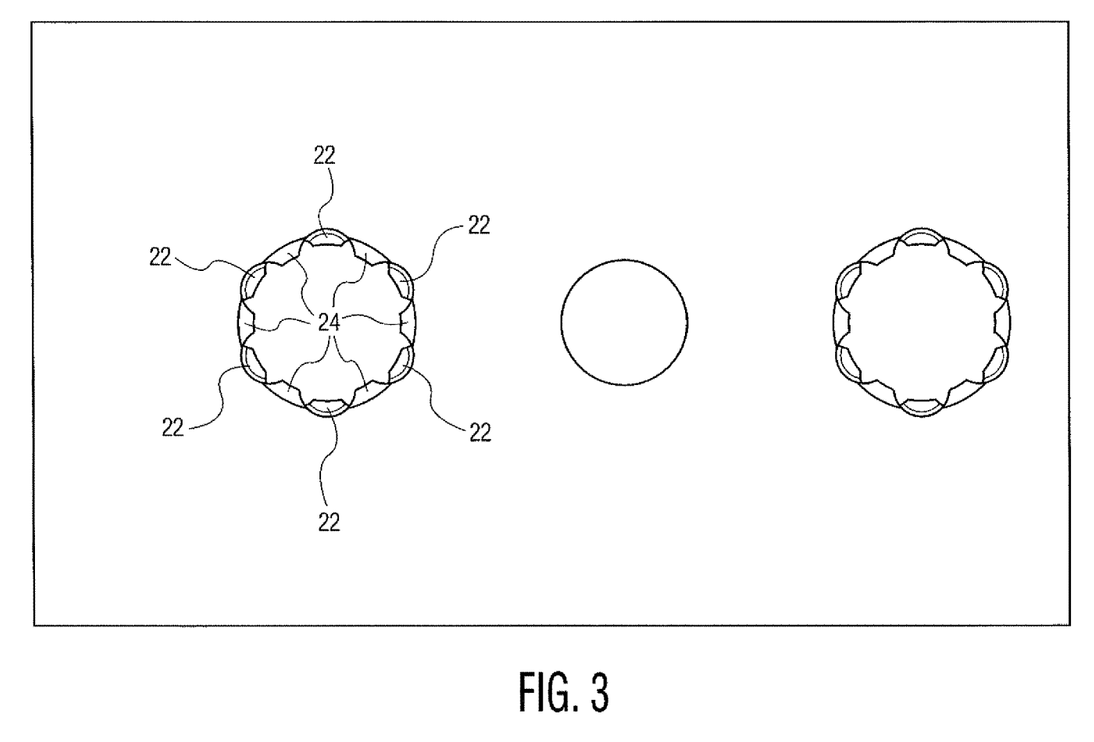
FIG. 3 is a bottom view of the plate of FIG. 1 with a similar focus on the two plate holes as in FIG. 2.
Figure 4:
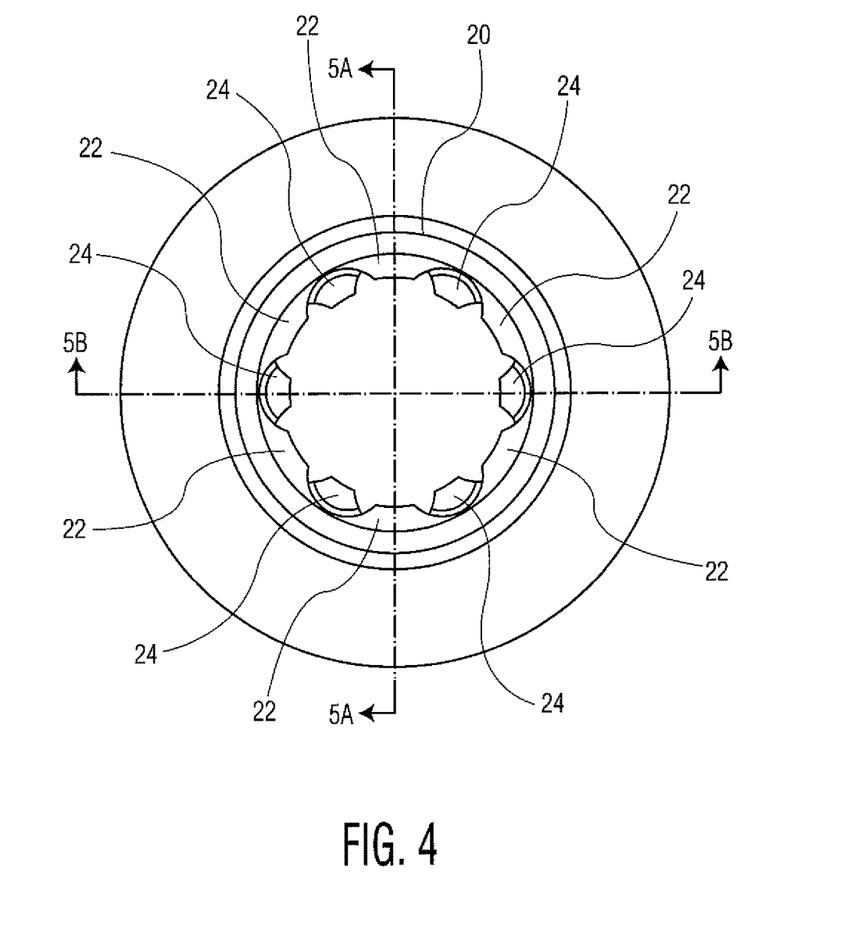
FIG. 4 is a top view focusing on a single plate/bone screw hole from the plate of FIG. 1.

With reference to FIG. 1, the present invention is directed to a bone plate 10 that includes a plurality of bone screw holes 12. As shown in FIG. 1, bone plate 10 also includes a series of other holes 14, which may be designed to receive different types of bone screws, k-wires, or the like, or in the case of the plate of FIG. 1, allows for the plate to be fit into a test fixture. Although shown as a straight plate with a rectangular shape, plate 10 may be designed to cooperate with different anatomical features of the body. For instance, plate 10 may be designed for placement on the distal radius, and therefore may include a head portion and a shaft portion (not shown). In any event, as will be readily apparent from the remaining description, the focus of the present invention is on bone screw holes 12, which are to be included in any such plate design. It is to be understood that the plates may include any number of bone screw holes 12, according to their specific intended use.

Figure 10:
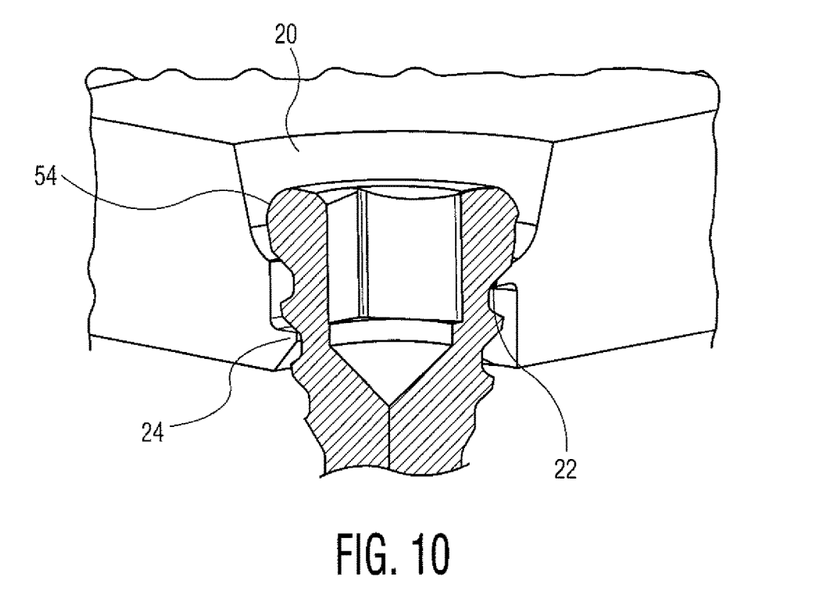
FIG. 10 is a cut away view depicting the bone screw of FIG. 9 placed within a bone screw hole of FIG. 4.

As is shown in FIGS. 2 through 6 in additional detail, hole 12 includes a countersink 20, a plurality of upper lips 22 and a plurality of lower lips 24. Countersink 20 is designed, as is shown in FIG. 10, to cooperate with a portion 54 of the head 52 of a bone screw 50, to both facilitate and limit polyaxial movement of the screw with respect to the plate. In particular, both countersink 20 and portion 54 are curved so as to allow for articulation of the two components with respect to one another through a range of angles, e.g., up to fifteen degrees in all directions around hole 12. Of course, the range of allowable polyaxial rotation can vary, including greater and less than the fifteen degrees allowed by the embodiment shown in FIG. 10. In addition, hole 12 is sized such that shank 58 of screw 50 is able to move a certain distance along with the articulation of head 52 (e.g., 15 degrees of rotation).

Figure 5A:
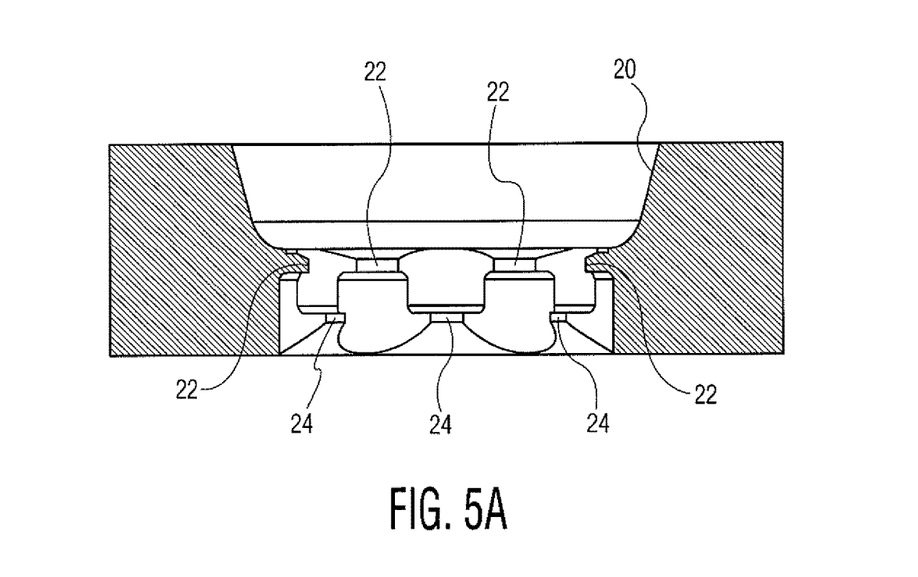
FIG. 5A is a cross-sectional view of the bone screw hole of FIG. 4 along a line B-B.
Figure 5B:
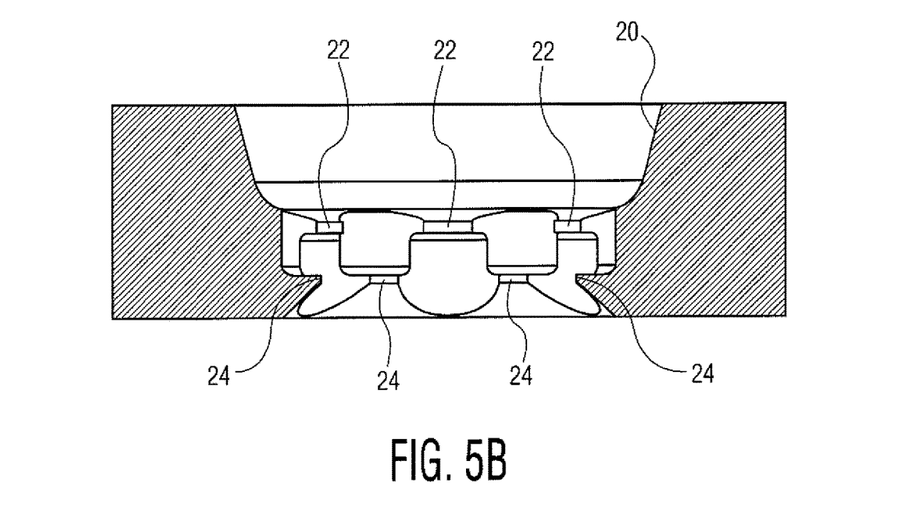
FIG. 5B is another cross-section of the bone screw hole of FIG. 4 along a line C-C.
Figure 6:
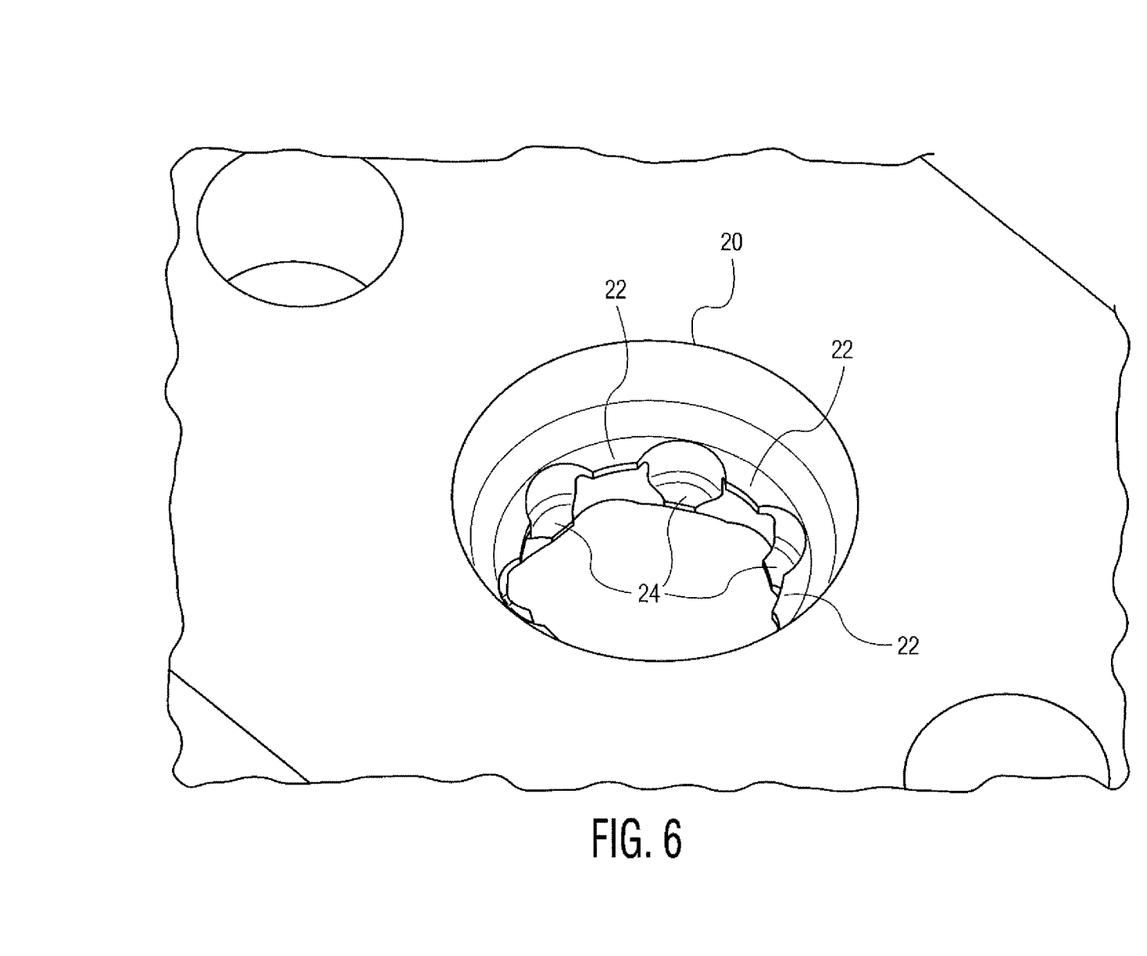
FIG. 6 is a top perspective view of the bone screw hole of FIG. 4.
Figure 7:
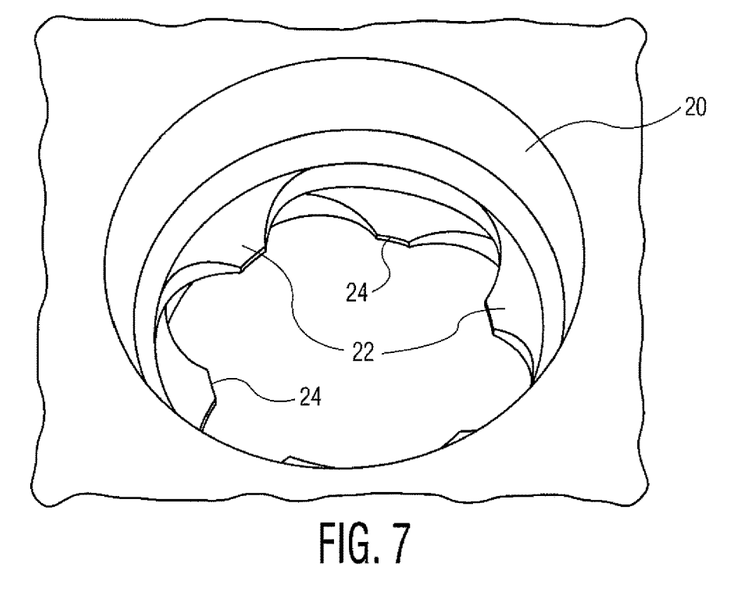
FIG. 7 is a top perspective view of a bone screw hole according to another embodiment of the present invention.
Figure 8:
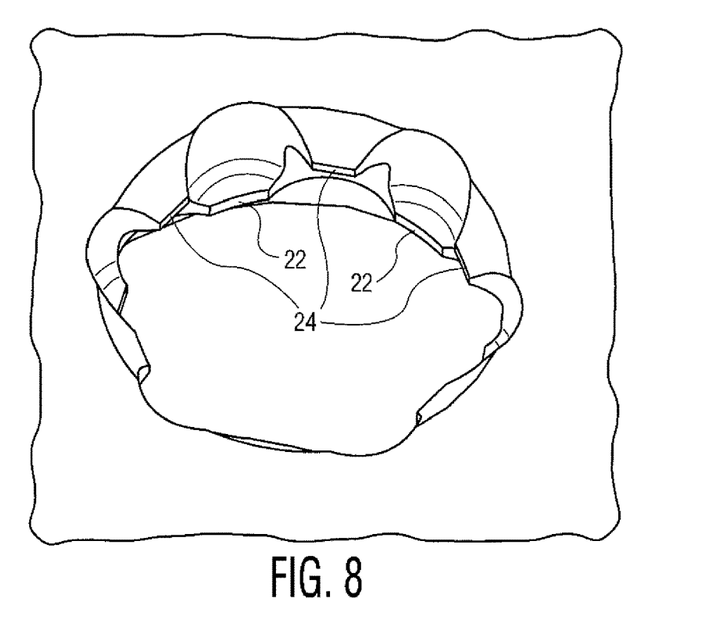
FIG. 8 is a bottom perspective view of the bone screw hole of FIG. 7.
Figure 9:
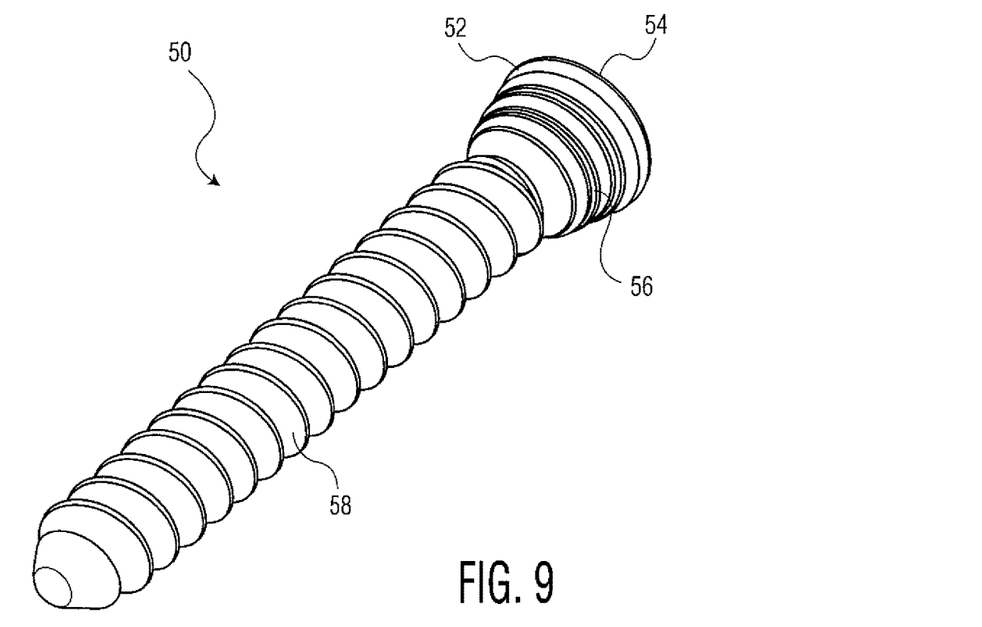
FIG. 9 is a perspective view of a bone screw for use with the bone plate of FIG. 1 and the bone screw hole of FIG. 4.

Upper lips 22 and lower lips 24 are situated circumferentially around hole 12 in an offset manner from one another so that they are not stacked vertically, but rather extend between one another in the axial direction. This is best shown in FIGS. 2 through 8. The lips are also spaced axially from one another so that there is a space therebetween, which is best shown in FIGS. 5A and 5B. As will be discussed more fully below, threaded portion 56 of head 52 of screw 50 is ultimately disposed within this space. In a preferred embodiment, upper lips 22 are arranged at 0°, 60°, 120°, 180°, 240° and 300°, while lower lips 24 are located at 30°, 90°, 150°, 210°, 270° and 360°. However, it is to be understood that the lips can be arranged at any orientation with respect to each other or hole 12. For instance, FIGS. 7 and 8 depict an embodiment hole 12 that includes four of each of upper lips 22 (situated at 0°, 90°, 180° and 270°) and lower lips 24 (situated at 45°, 135°, 225° and 315°).

As is shown in FIG. 10, placement of screw 50 through hole 12 results in a threaded portion 56 being captured between lips 22 and 24. This acts to prevent back out of the screw from the plate. Screw 50 may also be placed in hole 12 at a variety of angles, while still achieving the desired function. In fact, the configuration of lips 22 and 24, as well as the remainder of hole 12 allows for screw 50 to be held in place in a plurality of different angular orientations. The angled nature of lips 22 and 24 (best shown in FIGS. 5A-8) not only aids in such placement, but also makes the placement of threaded portion 56 easier to accomplish. As shown, the lips are effectively ramp-shaped (i.e., tapering towards a center of the hole) so as to make passing screw 50 through hole 12 easier. It is noted that the size of shank 58 of screw 50 must be sized to allow for the polyaxial movement of the screw within hole 12.

In certain embodiments, plate 10 and screw 50 can be constructed of the same material. Upper and lower lips 22, 24 act as somewhat weakened sections, and either deform or deflect upon placement of screw 50 in hole 12. The fact that threaded section 56 may include threads that are significantly stronger than the thinner lips 22, 24 may facilitate this deformation or deflection. In addition, it is contemplated that the plate may be constructed of a softer material than the screw, thereby further facilitating the deformation and/or deflection of the lips upon placement of the screw. The particular embodiment shown depicts a conically threaded head portion 56 of screw 50 which allows for 15° of rotation of the screw with respect to the plate. Of course, other screw hole/screw shapes/designs can be employed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate comprising:
    a body having upper and lower surfaces and an inner surface extending therebetween, the inner surface defining a bone screw hole, the inner surface having a plurality of first lips and a plurality of second lips, each of the lips of the first lips having a radially inward edge remote from the inner surface of the bone screw hole and side edges extending therebetween, the side edges being concave so as to form a concave depression between each of the lips of the first lips,
    wherein the first lips are closer to the upper surface than the second lips such that the first lips form a first row and the second lips form a second row, the first and second rows being vertically offset from each other along a longitudinal axis of the bone screw hole such that the first and second rows are in respective first and second planes transverse to the longitudinal axis of the bone screw hole such that the second row and corresponding second plane are offset relative to the first row and corresponding first plane, and
    wherein the first and second lips are circumferentially offset around the longitudinal axis of bone screw hole such that each of the lips of the second row are aligned with a corresponding depression of the first row.

2. The bone plate of claim 1, wherein the first and second lips include ramped surfaces.

3. The bone plate of claim 1, wherein the bone screw hole further includes a countersink.

4. A system comprising:
    the bone plate of claim 1; and
    a bone screw having a head and a shank.

5. The system of claim 4, wherein the bone screw is a harder material than bone plate.

6. The system of claim 5, wherein the head is a harder material than the first and second lips.

7. The system of claim 4, wherein placement of the bone screw through the bone plate results in a deformation or deflection of the first and second lips.

8. A bone plate system comprising:
    a body having a surface defining a bone screw hole through the body, the surface including a plurality of upper and lower lips, each of the lips of the upper lips having a radially inward edge remote from the surface of the bone screw hole and side edges extending therebetween, the side edges being concave such that each lip of the upper lips is narrower near the inward edge thereof than near the inner surface of the bone screw hole, wherein the first lips form a first row of lips and the second lips form a second row of lips, the first and second rows of lips being vertically offset from each other along a longitudinal axis of the bone screw hole such that the first row of lips is in a first plane transverse to the longitudinal axis of the bone screw hole and the second row of lips is in a second plane offset from the first plane and transverse to the longitudinal axis of the bone screw hole; and a bone screw having a head and a shank, wherein the head deforms or deflects the upper and lower lips.

9. The bone plate system of claim 8, wherein the upper and lower lips are offset from each other around the bone screw hole.

10. The bone plate system of claim 9, wherein the upper and lower lips are positioned about a central axis of the bone screw hole and are offset thirty degrees from each other about the central axis.

11. The bone plate system of claim 9, wherein the first and second lips do not overlap each other in a horizontal plane.

12. The bone plate system of claim 9, wherein the first and second lips partially overlap each other in a horizontal plane.

13. The bone plate of claim 8, wherein the first and second lips include ramped surfaces.

14. The bone plate of claim 8, wherein the bone screw hole further includes a countersink.

15. The system of claim 8, wherein the bone screw is a harder material than bone plate.

16. The system of claim 15, wherein the head is a harder material than the upper and lower lips.

17. A bone plate system comprising:

a body having an inner surface, the inner surface defining a bone screw hole formed through the body, the inner surface having a plurality of ramped upper and lower lips extending therefrom, each of the lips of the upper lips having a radially inward edge remote from the surface of the bone screw hole and side edges extending therebetween, the side edges being concave so as to form scalloped regions between each of the lips of the upper lips, wherein the upper lips form a first row and the lower lips form a second row being vertically offset from each other along the longitudinal axis of the bone screw hole, wherein the first row is in a first plane transverse to the longitudinal axis of the bone screw hole and the second row is in a second plane offset from the first plane and transverse to the longitudinal axis of the bone screw hole; and a bone screw having a head and a shank, wherein the head deforms or deflects the upper and lower lips upon insertion of the bone screw in the bone screw hole.

* * * * *